United States Patent [19]

Mondelo

[11] Patent Number: 4,870,178

[45] Date of Patent: Sep. 26, 1989

[54] PROCESS FOR THE OBTENTION OF THE ETHYL ESTER OF THE APOVINCAMINIC ACID

[75] Inventor: Fernando C. Mondelo, Madrid, Spain

[73] Assignee: Covex, S.A., Madrid, Spain

[21] Appl. No.: 929,608

[22] Filed: Nov. 10, 1986

[30] Foreign Application Priority Data

Nov. 20, 1985 [ES] Spain .................................. 549105

[51] Int. Cl.$^4$ .......................................... C07D 471/04
[52] U.S. Cl. ...................................................... 546/51
[58] Field of Search ......................................... 546/51

[56] References Cited

FOREIGN PATENT DOCUMENTS 2253750 11/1972 Fed. Rep. of Germany ........ 546/51

OTHER PUBLICATIONS

Kim et al., Chem Abstracts: vol. 97; 143998v (1982).
Richter et al, Chem Abstracts, vol. 76, 1972; 34460j.
March, J., Adv. Org. Chem., pp. 363-367.

Primary Examiner—Mary C. Lee
Assistant Examiner—J. Richter
Attorney, Agent, or Firm—Ladas & Parry

[57] ABSTRACT

A process for preparing the ethyl ester of apovincaminic acid by reacting the apovincaminic acid with ethyl alcohol and in the presence of aminopyridine and trinitrobenzene derivatives. The product is useful as a cerebral vasodilator.

4 Claims, No Drawings

PROCESS FOR THE OBTENTION OF THE ETHYL ESTER OF THE APOVINCAMINIC ACID

The present invention refers to a new process for the preparation of the ethyl ester of the apovincaminic acid, of general formula (I):

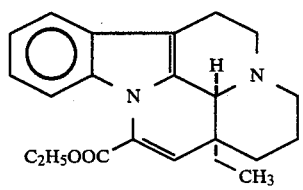

As indicated in DE 2,253,750 the ethyl ester of apovincamic acid is a cerebral vasodilator. Thus, a simple process for isolating the substance in greater yield is medically useful.

Some processes for the obtention of this substance are already known, as for example in German Pat. No. 2,253,750 and No. 2,265,138 and in Austrian Pat. No. 322,118, but all of them require a long reacting time, are almost always performed at high temperatures, the purification thereof is slow and complicated and the yield ranges between the 50 and the 85% of the theoretic one.

By means of the process according to the present invention, the aforementioned disadvantages are widely overcome, as it has a yield of about the 92%, it is performed at room temperature, the purification is a simple one and the reacting time is short.

The process according to the present invention consists of reacting at room temperature the apovincaminic acid, of general formula (II):

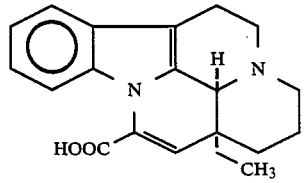

with ethyl alcohol in the presence of 2-fluoro-1,3,5-trinitrobenzene and 4-dimethylaminopyridine as esterifying agents.

The reaction is performed at room temperature and the time needed to complete it is of 3 to 5 hours.

The substance (I) was characterized by the melting point, IR and NMR spectra and quantitative elemental analysis thereof.

The following example illustrates the details of the process according to the invention.

EXAMPLE

A solution of 5 g of apovincaminic acid and 3.6 g of 2-fluoro-1,3,5-trinitrobenzene in 100 ml of acetonitrile is added to 3.6 g of 4-dimethylaminopyridine and 5 ml of absolute ethanol. The reaction mixture is stirred at room temperature for 4 hours. Once this time has elapsed, the insoluble salts are filtered off. The solvent is evaporated under vacuum and the residue is purified by filtration through a silica gel column, using 1,2-dichloroethane as elutant. The solvent is evaporated under vacuum and the solid residue is recrystallized in absolute ethanol. 4.75 g of ethylapovincaminate are thus obtained with a yield of the 92% of the theoretic one; melting point: 148°–151° C., /α/60, D= +114,3° (pyridine, c=1).

The amendments which might be introduced in the above described process and which do not alter the characteristic essence thereof, will be understood as included in the following claims.

I claim:

1. A process for preparing the ethyl ester of apovincaminic acid, of the formula:

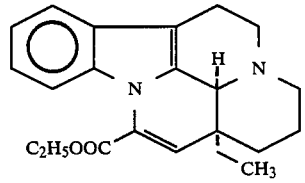

comprising reacting apovincaminic acid with ethyl alcohol, at room temperature in the presence of 2-Fluoro-1,3,5-trinitrobenzene and 4-Dimethylaminopyridine, for 3–5 hours in acetonitrile as solvent.

2. A process, as in claim 1 wherein said process has a yield of the ethyl ester of apovincamic acid of about 92%.

3. A process, as in claim 2 wherein the time of reaction comprises 4 hours.

4. A process, as in claim 1 wherein after the reaction is completed the process further comprises filtering off the insoluble salts, evaporating the solvent, under vacuum, purifying the residue by filtration through silica gel using 1,2-dichloroethane as eluant, evaporating off the solvent under vacuum, and recrystallizing the solid residue in absolute ethanol.

* * * * *